(12) United States Patent
Stensrud

(10) Patent No.: US 9,920,003 B2
(45) Date of Patent: Mar. 20, 2018

(54) NON-IONIC AMPHIPHILES AND METHODS OF MAKING THE SAME

(71) Applicant: Archer Daniels Midland Company, Decatur, IL (US)

(72) Inventor: Kenneth Stensrud, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/502,849

(22) PCT Filed: Feb. 9, 2015

(86) PCT No.: PCT/US2015/045848
§ 371 (c)(1),
(2) Date: Feb. 9, 2017

(87) PCT Pub. No.: WO2016/028865
PCT Pub. Date: Feb. 25, 2016

(65) Prior Publication Data
US 2017/0233337 A1 Aug. 17, 2017

Related U.S. Application Data

(60) Provisional application No. 62/039,091, filed on Aug. 19, 2014, provisional application No. 62/093,092, filed on Dec. 17, 2014.

(51) Int. Cl.
| | |
|---|---|
| *C07C 69/52* | (2006.01) |
| *C07C 309/68* | (2006.01) |
| *C07C 59/105* | (2006.01) |
| *C07C 59/285* | (2006.01) |
| *C07C 67/14* | (2006.01) |
| *C07C 303/30* | (2006.01) |
| *C07C 219/06* | (2006.01) |
| *C07C 213/08* | (2006.01) |

(52) U.S. Cl.
CPC .......... *C07C 309/68* (2013.01); *C07C 59/105* (2013.01); *C07C 59/285* (2013.01); *C07C 67/14* (2013.01); *C07C 213/08* (2013.01); *C07C 219/06* (2013.01); *C07C 303/30* (2013.01)

(58) Field of Classification Search
CPC ... C07C 213/08; C07C 219/06; C07C 303/30; C07C 309/68; C07C 59/105; C07C 59/285; C07C 67/14; C07C 307/20
See application file for complete search history.

(56) References Cited

U.S. PATENT DOCUMENTS 4,749,694 A * 6/1988 Fix ...................... A61K 9/0031
514/200

* cited by examiner

*Primary Examiner* — Yevgeny Valenrod
*Assistant Examiner* — Blaine G Doletski
(74) *Attorney, Agent, or Firm* — William B. Miller

(57) ABSTRACT

Sugar-derived tetrol, non-ionic amphiphilic amine-esters are prepared facilely and efficaciously in a few steps. The process is initiated by the esterification of a sugar-derived tetrol with a fatty acid chloride, then, undergoing triflate esterification followed by nucleophilic displacement of the aforementioned hydrophilic amine. Each synthetic pathway is efficient and affords modest to high yields of target amphiphiles, which are valorized as practicable surfactant surrogates to petroleum incumbents.

4 Claims, 13 Drawing Sheets

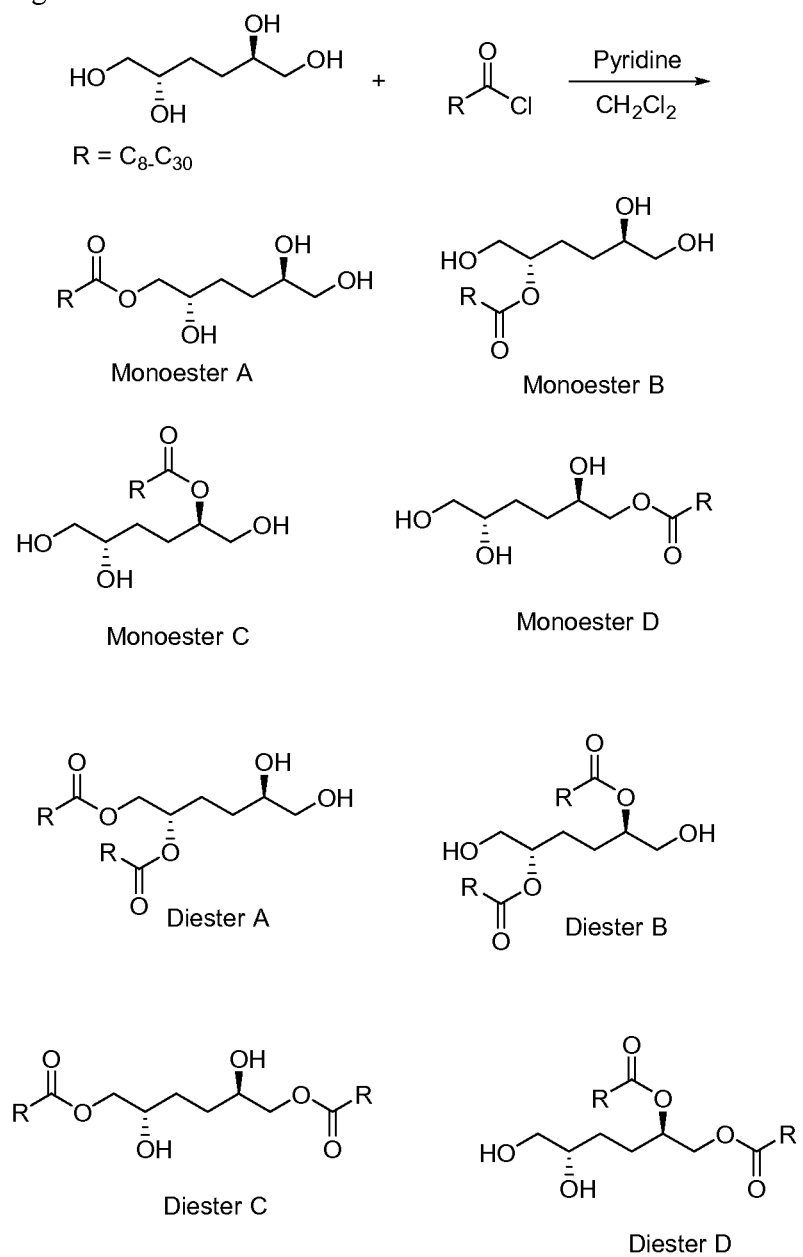
Figure 5A: General scheme for HTO esterification:

Figure 5B: General scheme for HTO esterification continued…
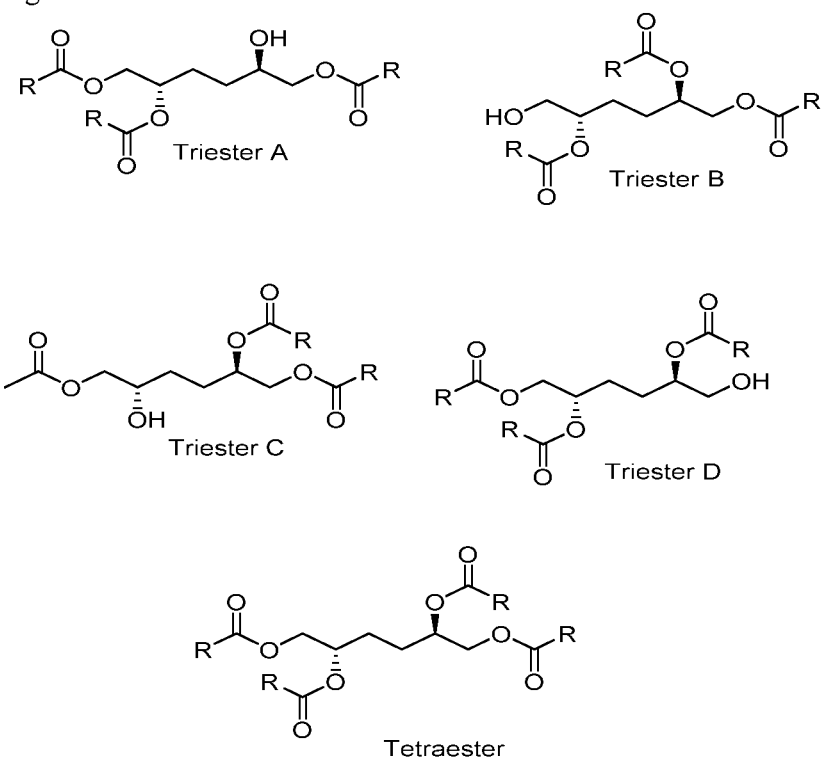

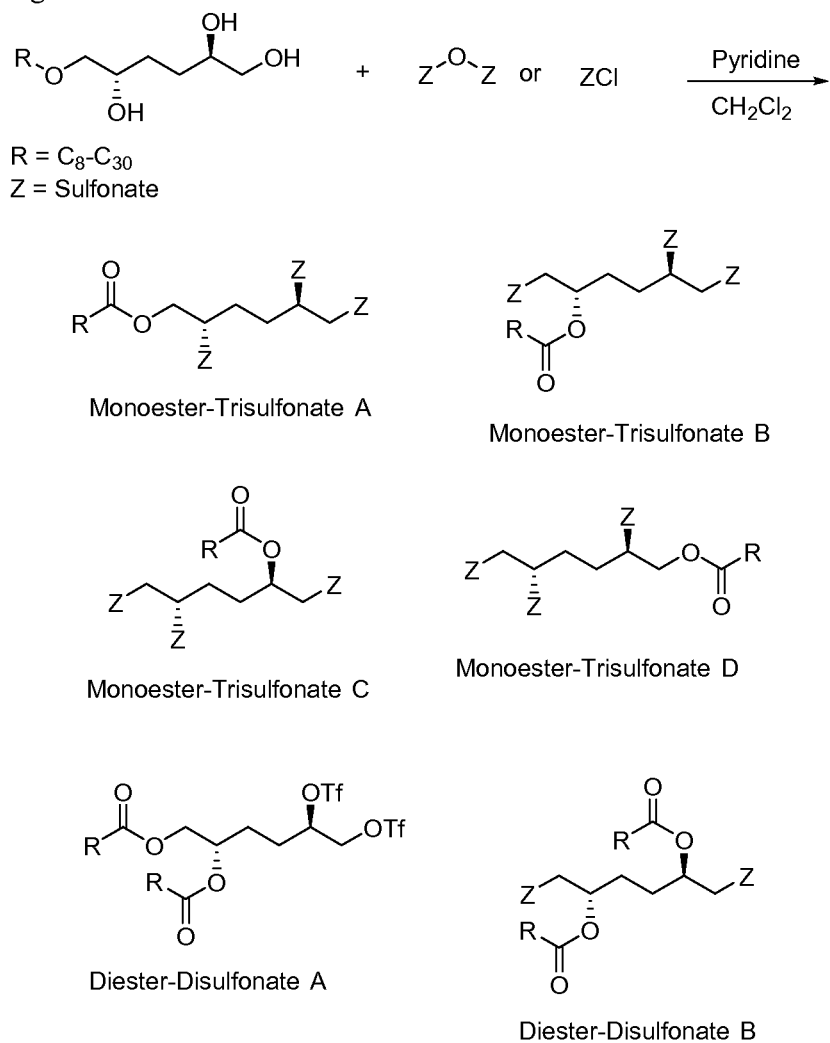
Figure 6A: General scheme for sulfonation of HTO-esters

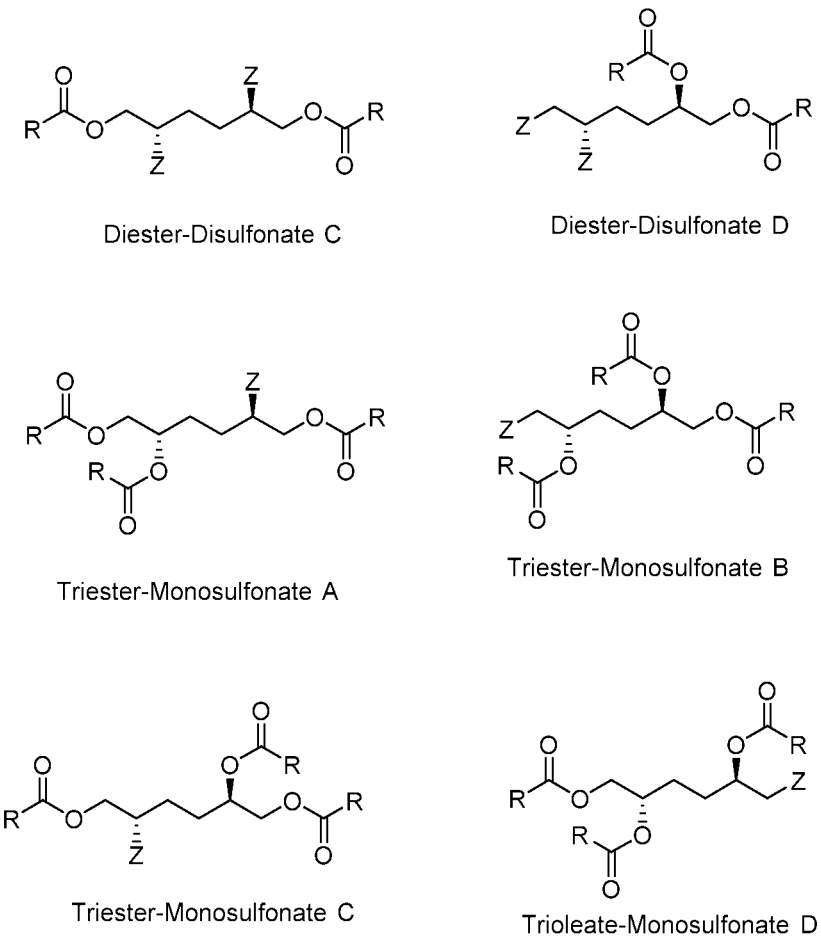

Figure 7: General scheme for amphipathic HTO variants continued...
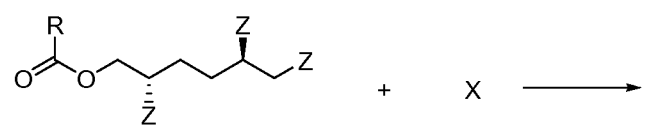
R = $C_8$-$C_{30}$
Z = Sulfonate
X = $NH_2(CH_2CH_2)_nNH(CH_2CH_2)_nOH$
    $NH_2(CH_2CH_2)_nO(CH_2CH_2)_nOH$
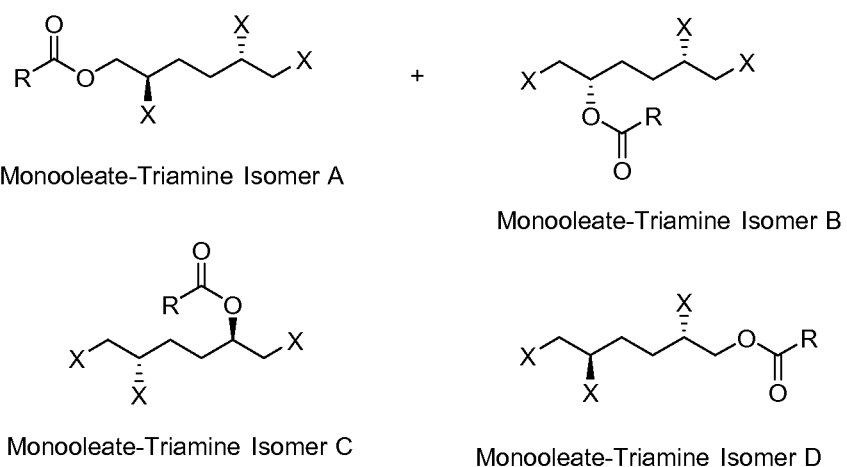
Monooleate-Triamine Isomer A
Monooleate-Triamine Isomer B
Monooleate-Triamine Isomer C
Monooleate-Triamine Isomer D

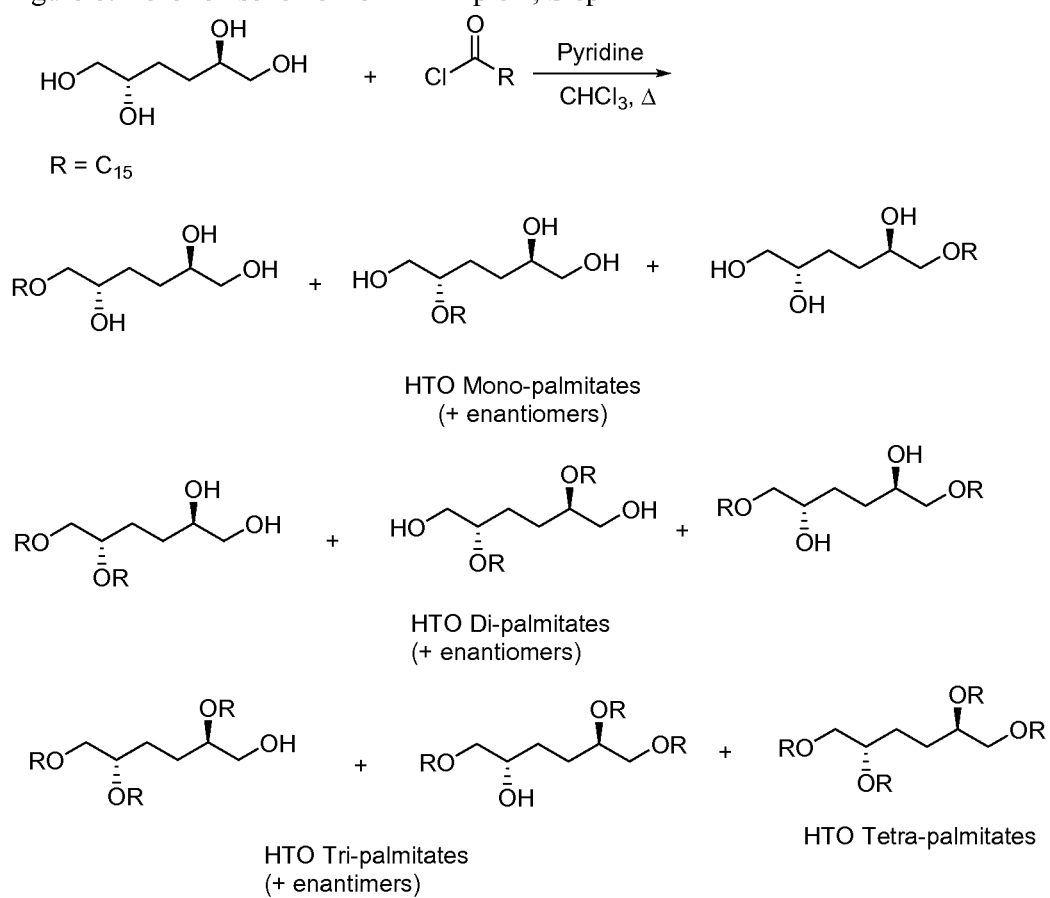
Figure 8: Reaction scheme from Example 1, Step 1

Figure 9: Reaction Scheme from Example 1, Step 2
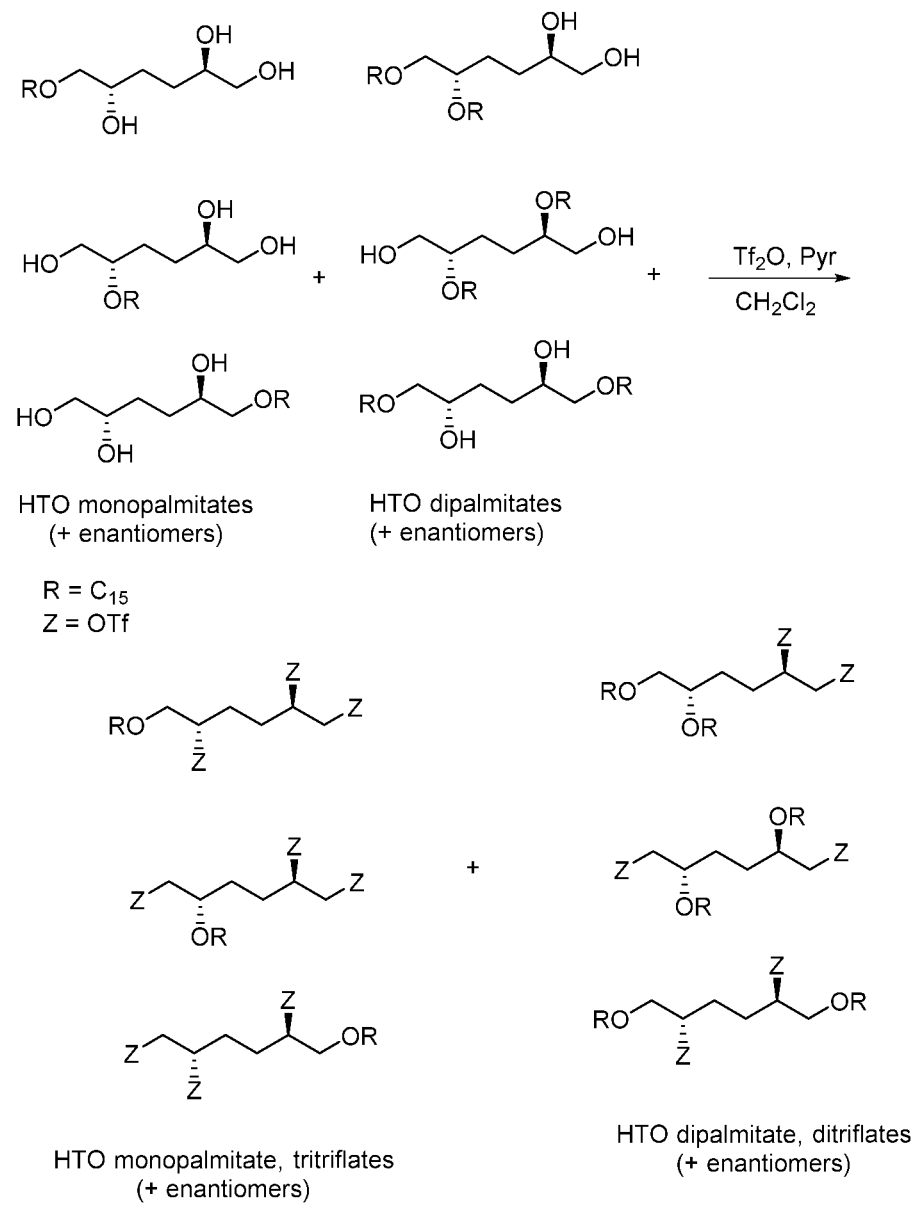

Figure 10: Reaction Scheme from Example 1, Step 3
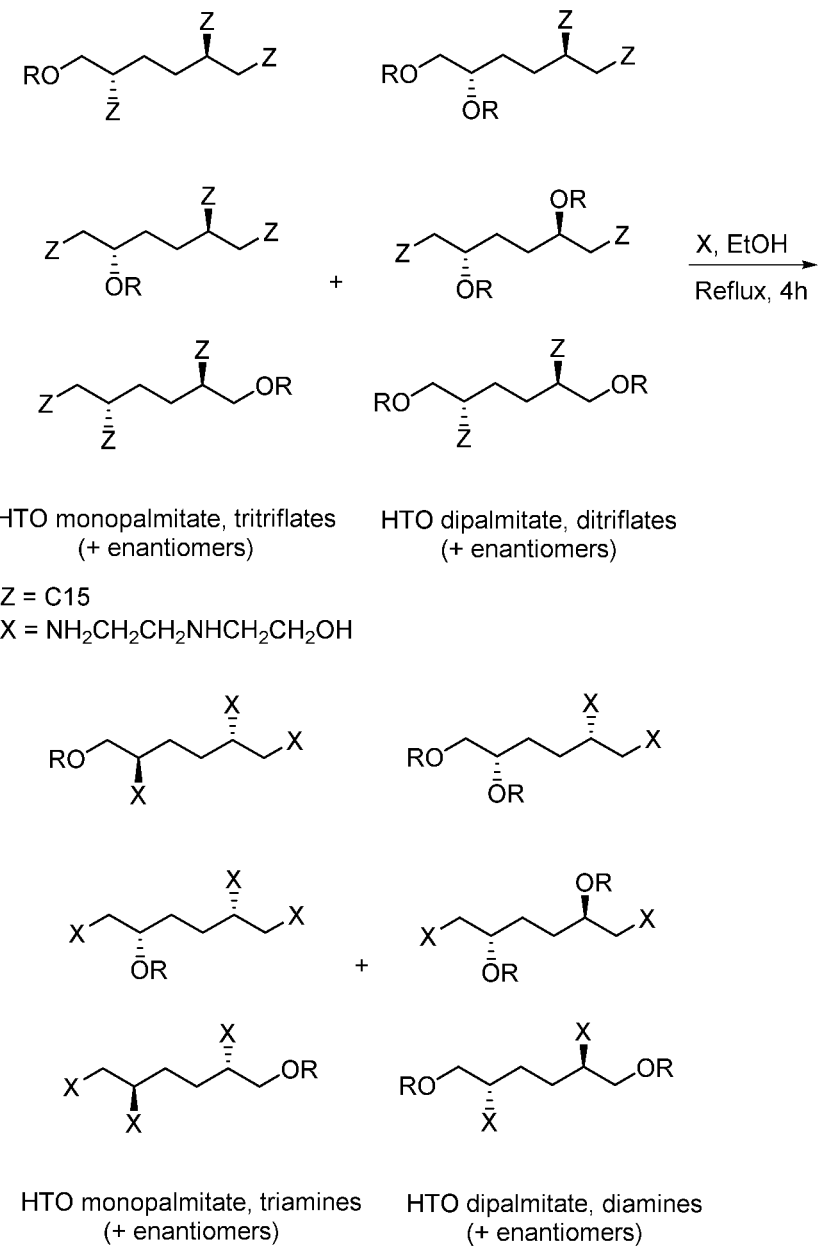
HTO monopalmitate, tritriflates (+ enantiomers)
HTO dipalmitate, ditriflates (+ enantiomers)
Z = C15
X = NH$_2$CH$_2$CH$_2$NHCH$_2$CH$_2$OH
HTO monopalmitate, triamines (+ enantiomers)
HTO dipalmitate, diamines (+ enantiomers)

Figure 11: Reaction Scheme from Example 2, Step 1
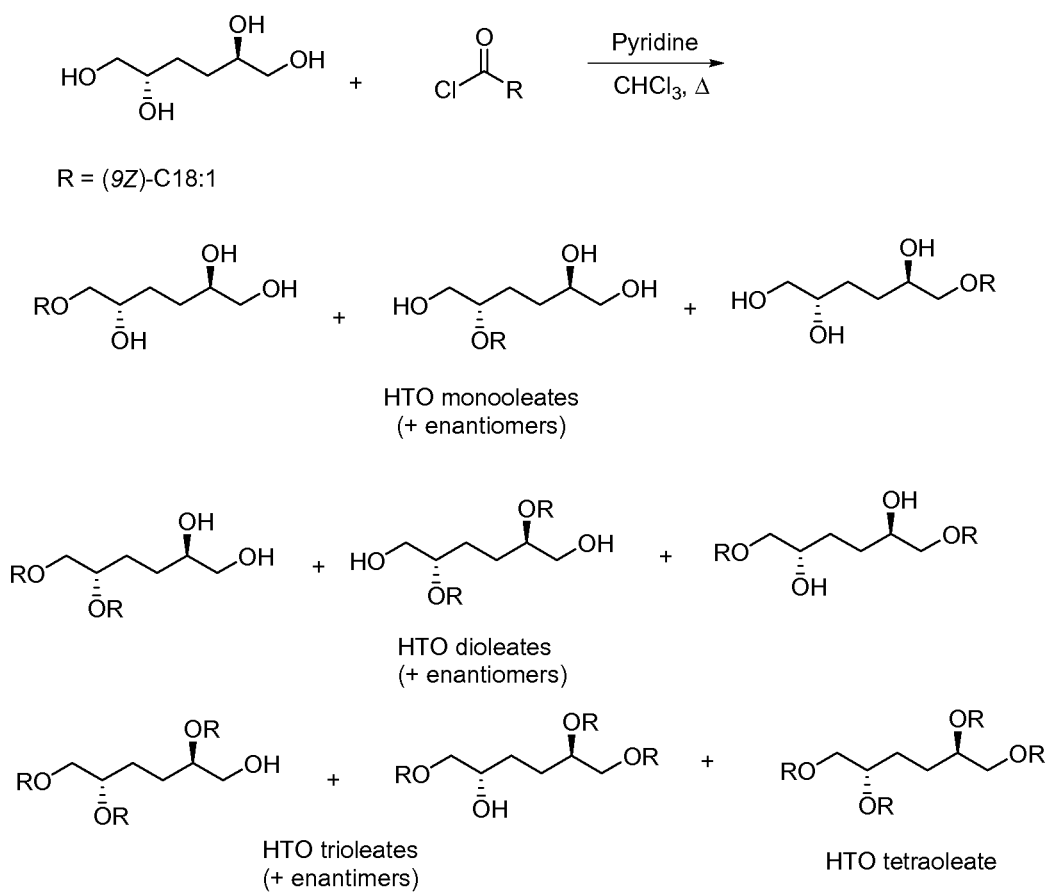

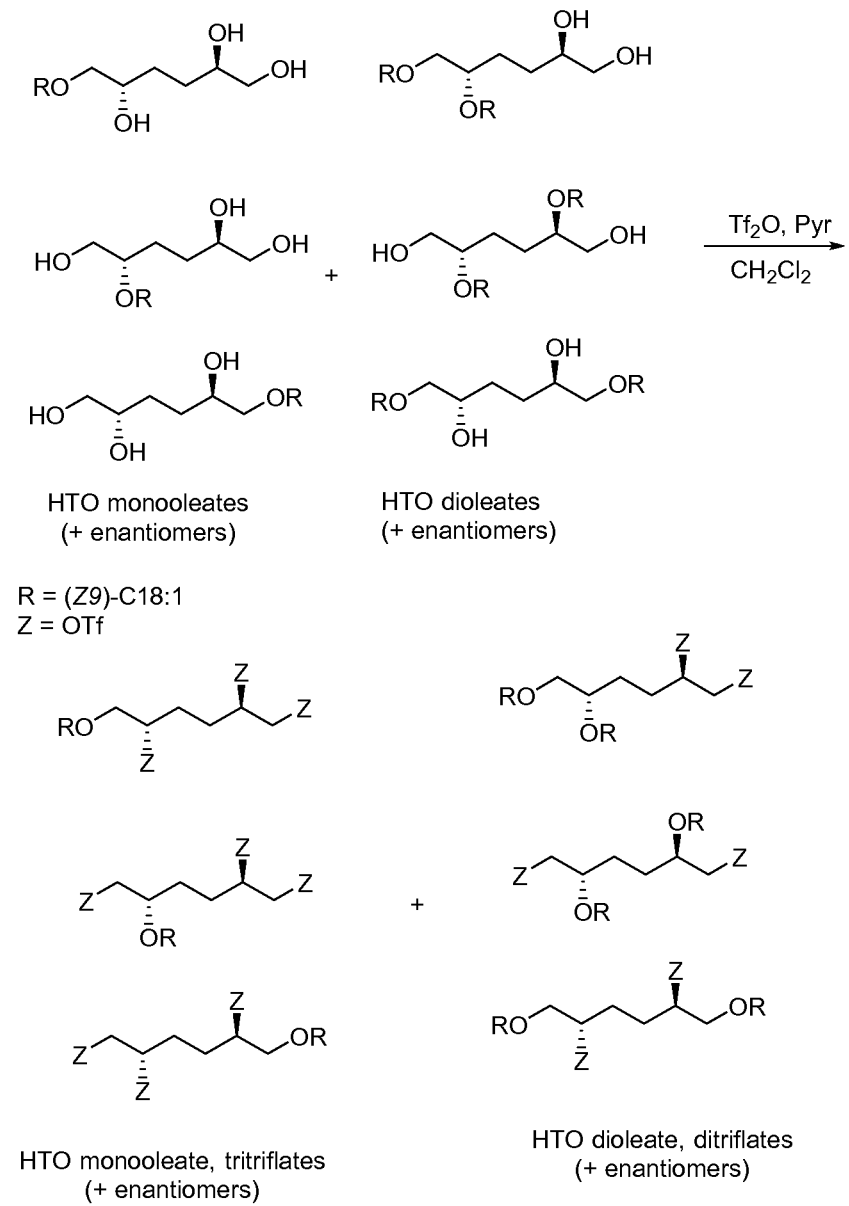
Figure 12: Reaction Scheme from Example 2, Step 2

Figure 13: Reaction Scheme from Example 2, Step 3
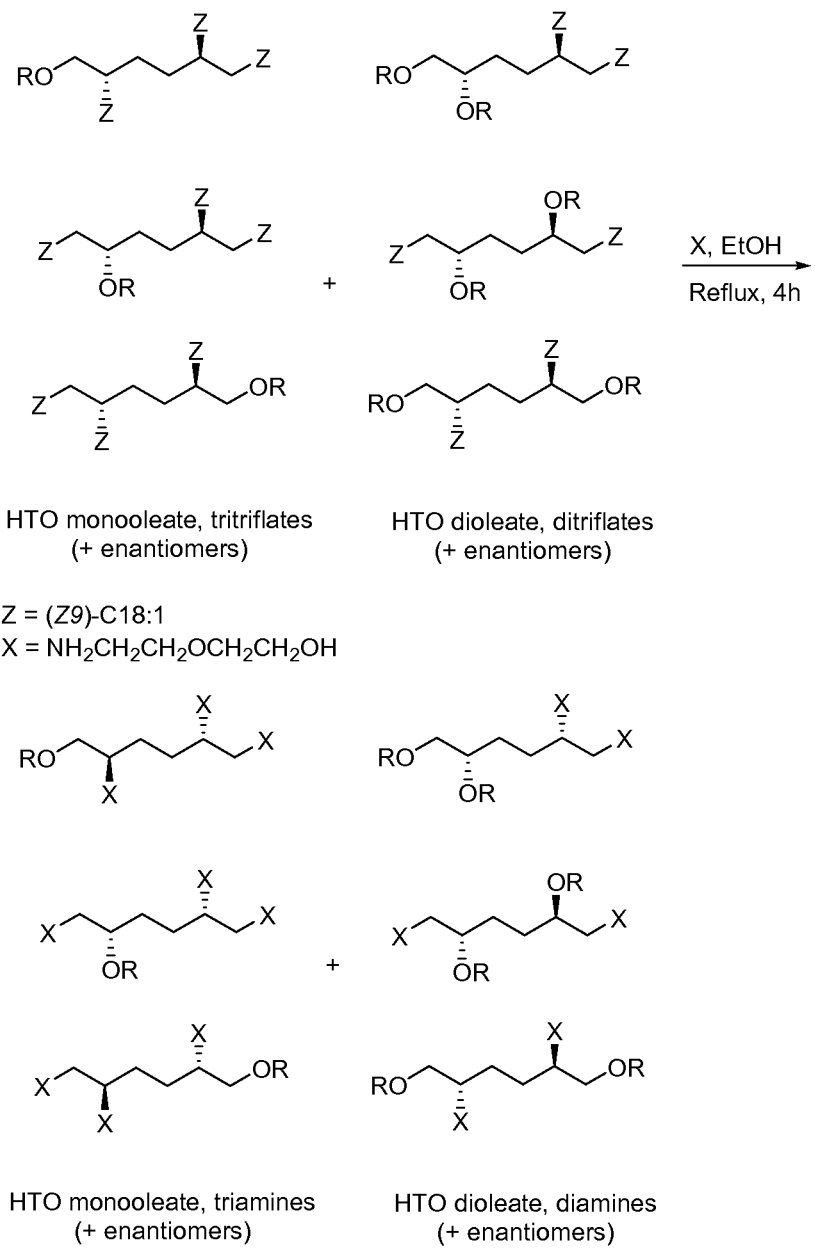

NON-IONIC AMPHIPHILES AND METHODS OF MAKING THE SAME

CROSS REFERENCE TO RELATED APPLICATION

The present application is a national stage entry of International Application No. PCT/US2015/045848, filed Aug. 19, 2015, which itself claims priority to the International Patent Application PCT/US2014/033580 and PCT/US2014/033581 both filed Apr. 10, 2014, and to U.S. provisional patent application Ser. No. 62/039,091, which was filed on Aug. 19, 2014, and U.S. provisional patent application Ser. No. 62/093,092, filed on Dec. 17, 2014, the contents of which are incorporated herein by reference in their entirety.

FIELD OF THE INVENTION

The present application relates to the preparation of amphiphilic compounds from bio-derived molecules. In particular, the present disclosure describes preparation of derivatives from a sugar-derived tetrol.

BACKGROUND OF THE INVENTION

The once plentiful petroleum reserves, which have served as the principal source of cheap, ubiquitous antecedents to most commodity chemicals for decades, are projected to peak over the next few years. Once achieved, the years following will manifest circumstances where supply is outstripped by demand, a corollary of which is a steady, unchecked price escalations of foods and other consumables. Thus, it is incumbent for scientists around the world to search for more sustainable surrogates, particularly those derived from biomass. A subdivision of biomass is a genre of diverse, panoptic materials termed carbohydrates or sugars (i.e., hexoses and pentoses), that can readily be transformed into polytropic derivatives.

One such derivative, readily made from the regioselective dehydroxylation of sorbitol, a $C_6$ sugar alcohol that is produced on the industrial scale primarily from the reduction of glucose, is 1,2,5,6-hexanetetrol.

1,2,5,6-hexanetetrol (HTO) is a rare, tetrafunctional substrate, auspicious as a precursor to copious derivatives that, owing to their agricultural production, can be deemed as "green" or "renewable". The intrinsic, multiple sites of chirality is a feature of particular appeal to the medicinal chemist, as the vast majority of pharmaceuticals contain one or more stereocenters. By virtue of the prodigious quantities isolated from corn and other plant materials, sorbitol provides an enticing platform on which to perform such modifications, and furthermore permits the realization of useful derivatives economically.

The multiple alcohol moieties inherent in HTO can serve as nucleophiles in some aspects, and as sites for further functionalization in others. The present disclosure describes several derivatives of HTO useful as building blocks for further compounds, including amphiphilic compounds that are useful in a variety of applications.

SUMMARY OF THE INVENTION

The present disclosure describes the use of regioselectively dehydroxylated monosaccharides, particularly exemplified using the reduced hexane polyol 1,2,5,6 hexanetetrol (HTO), in the synthesis of non-ionic amphiphiles capable of being employed as green surfactants. In particular, the present disclosure pertains to a process for preparing bio-based amphiphiles from HTO.

The present describes that sugar alcohol and tetrol esters can be prepared by the following method: a) esterifying a reduced hexane polyol with a fatty acid chloride; then b) sulfonating the esterified hexane polyol with a sulfonating agent to form a sulfonated hexane ester, and c) displacing the sulfonate moiety that is a hydrophilic amine to generate an amphipathic amine-ester derivative.

One aspect of this disclosure describes an esterified reduced hexane polyol selected from the group consisting of:

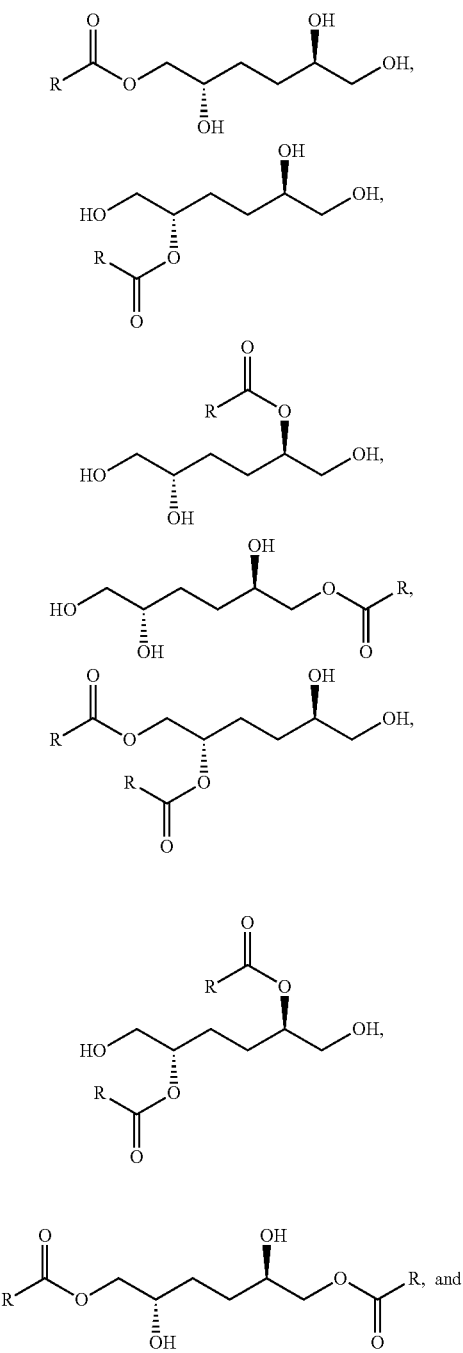

-continued

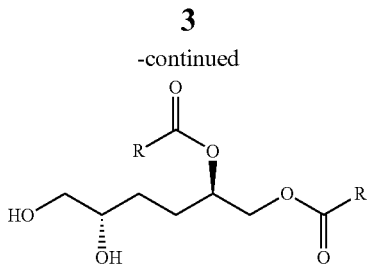

wherein R is a carbon side chain of a fatty acid. In certain, embodiments, the carbon side chain of the fatty acid is between 8 and 30 carbons.

Another aspect of this disclosure is a method of making an esterified reduced hexane polyol comprising contacting a reduced hexane polyol with a fatty acid chloride in the presence of a nucleophilic base. In certain embodiments, the fatty acid chloride is $C_8$-$C_{30}$. In further embodiments, the nucleophilic base is at least one of pyridine, dimethylaminopyridine, imidazole or a tertiary amine. In even further embodiments, the reduced hexane polyol is contacted with the fatty acid chloride at a temperature of from about 0° C. to about 50° C., more specifically at about 25° C.

Another aspect of this disclosure describes a sulfonated hexane ester compound selected from the group consisting of:

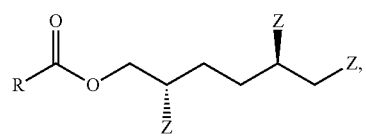

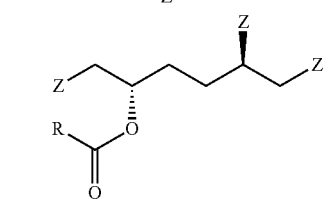

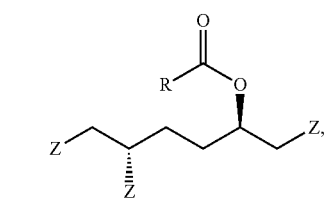

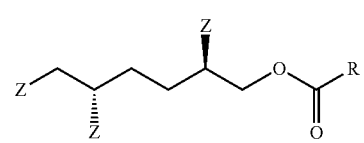

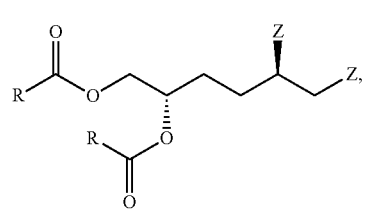

-continued

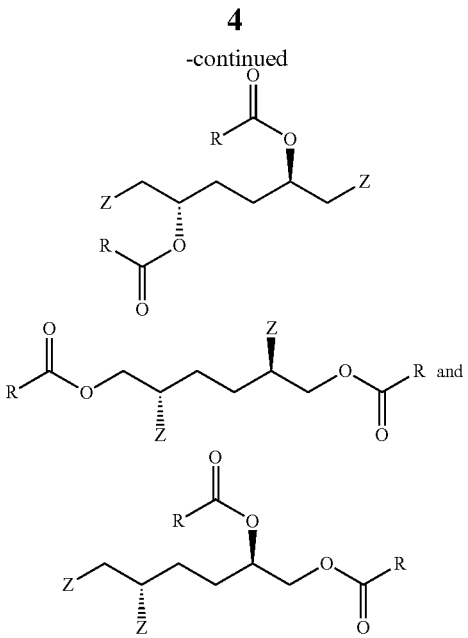

wherein R is a carbon side chain of a fatty acid and Z is a sulfonate ester moiety. In a certain embodiment, the carbon side chain of the sulfonated hexane ester is between 8 and 30 carbons. In further embodiments, the moiety of the sulfonated hexane ester is selected from the group consisting of p-toluenesulfonyl (tosyl), methanesulfonyl, (mesyl), ethanesulfonate (esyl), benzenesulfonate (besyl), p-bromobenzenesulfonate (brosyl), and triflouromethanesulfonic anhydride (triflate).

Another aspect of this disclosure is a method of making a sulfonated hexane ester comprising contacting an esterified reduced hexane polyol with a sulfonating agent to form the sulfonate ester moiety. In certain embodiments the sulfonating agent is selected from the group consisting of p-toluenesulfonyl (tosyl), methanesulfonyl, (mesyl), ethanesulfonate (esyl), benzenesulfonate (besyl), p-bromobenzenesulfonate (brosyl), and triflouromethanesulfonic anhydride (triflate).

In further embodiments, the contacting is done in the presence of an organic solvent selected from the group consisting of chloroform, tetrahydrofuran, acetone, benzene, diethyl ether, and methylene chloride. In exemplary embodiments, the sulfonated hexane ester compound is contacted with the sulfonating agent at a temperature of from about −20° C. to about 26° C., more specifically at about 0° C.

Another aspect of this disclosure describes an amphiphilic compound selected from the group consisting of:

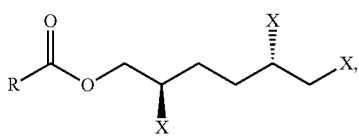

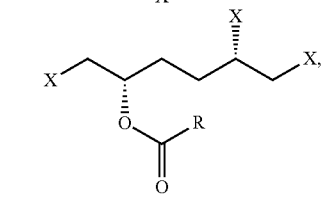

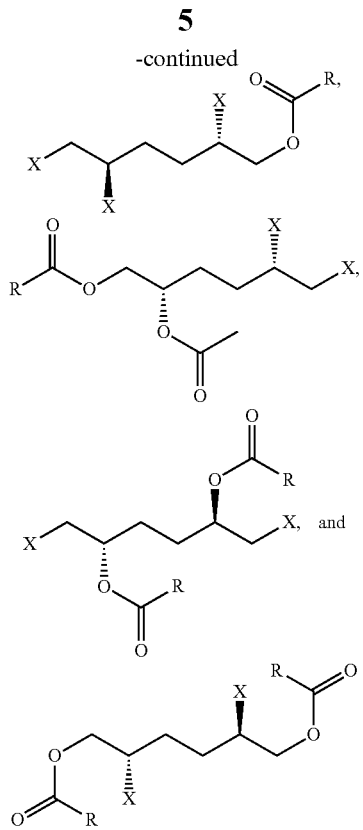

wherein R is a carbon side chain of a fatty acid and X is an organic substituent having sufficient hydrogen bonding capacity to make the compound amphiphilic. In certain embodiments, the amphiphilic compound has a carbon side chain with between 8 and 30 carbons.

An exemplary embodiment of this aspect is a method of making an amphiphilic compound comprising contacting a sulfonate ester moiety of a sulfonated hexane ester with a primary amine to displace said sulfonate ester moiety with the primary amine in the presence of polar solvent selected from the group consisting of dimethylsulfoxide, dimethylformamide, dimethylacetamide, N-methylpyrrolidone, acetonitrile, methanol, ethanol, and acetone. In certain embodiments, the sulfonate ester moiety is contacted with said primary amine at a temperature from about 30° C. to about 100° C., more specifically at about 50° C.

Additional features and advantages of the present synthesis process and material compounds will be disclosed in the following detailed description. It is understood that both the foregoing summary and the following detailed description and examples are merely representative of the invention, and are intended to provide an overview for understanding the invention as claimed.

BRIEF DESCRIPTION OF DRAWINGS

FIGS. 5A & B depict the general scheme for HTO esterification.

FIGS. 6A & B depict the general scheme for sulfonation of HTO-esters.

FIG. 7 depicts the general scheme for amphipathic HTO variants.

FIG. 8 depicts the preparation of HTO-palmitate amphiphiles as shown in Example 1, Reaction Scheme of Synthesis and isolation of HTO mono, di, tri and tetrapalmitates as seen in Step 1.

FIG. 9 depicts the preparation of HTO-palmitate amphiphiles as shown in Example 1, Reaction Scheme of Triflation of HTO mono and dipalmitates as seen in Step 2.

FIG. 10 depicts the preparation of HTO-palmitate amphiphiles as shown in Example 1, Reaction Scheme of AEEA-derivitized HTO mono and dipalmitates as seen in Step 3.

FIG. 11 depicts the preparation and isolation of HTO-oleate amphiphiles as shown in Example 2, Reaction Scheme of Synthesis and isolation of HTO mono, di, tri and tetraoleates as seen in Step 1.

FIG. 12 depicts the preparation and isolation of HTO-oleate amphiphiles as shown in Example 2, Reaction Scheme of Triflation of HTO mono and dioleates as seen in Step 2.

FIG. 13 depicts the preparation and isolation of HTO-oleate amphiphiles as shown in Example 2, Reaction Scheme of AEE derivitized HTO mono and dioleates as seen in Step 3.

DEFINITIONS

Figure 1:
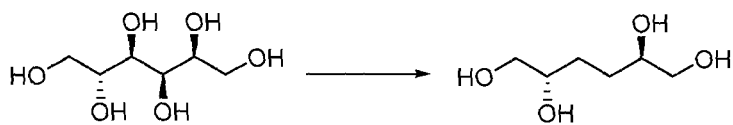
FIG. 1 depicts the reduction of sorbitol to 1,2,5,6-hexanetetrol.
Figure 2:
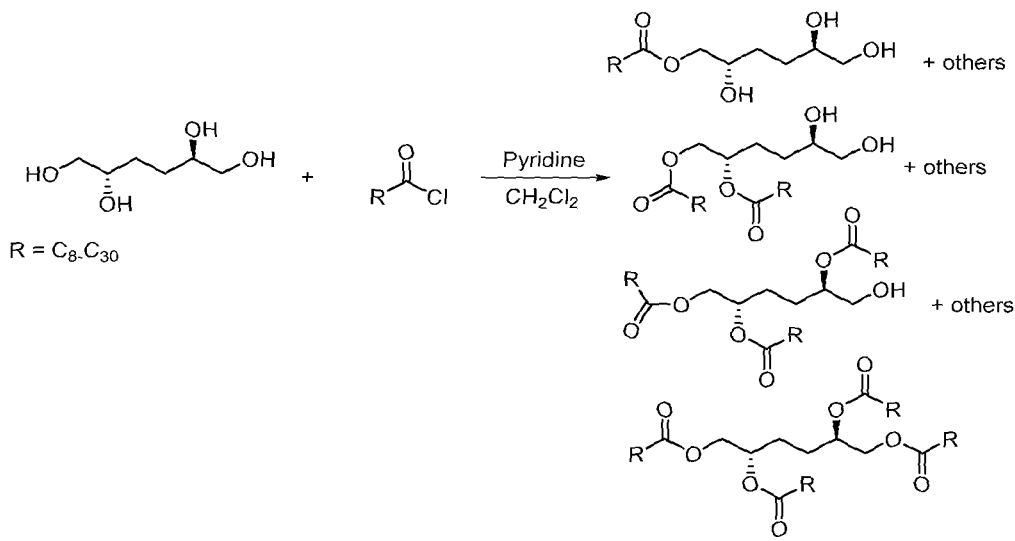
FIG. 2 depicts the acylation of 1 or 2 of the —OH moieties of 1,2,5,6-hexanetetrol with $C_8$-$C_{30}$ saturated or unsaturated acid chloride in the presence of a nucleophilic base.
Figure 3:
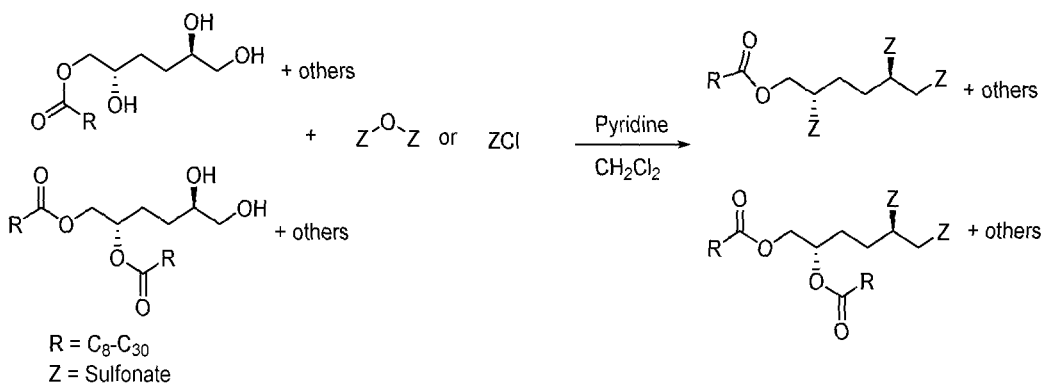
FIG. 3 depicts the sulfonation of vestigial —OH moieties of 1,2,5,6-hexanetetrol mono and di-esters with trifluoromethane-sulfonate (triflate), affording a potent nucleofuge.
Figure 4:
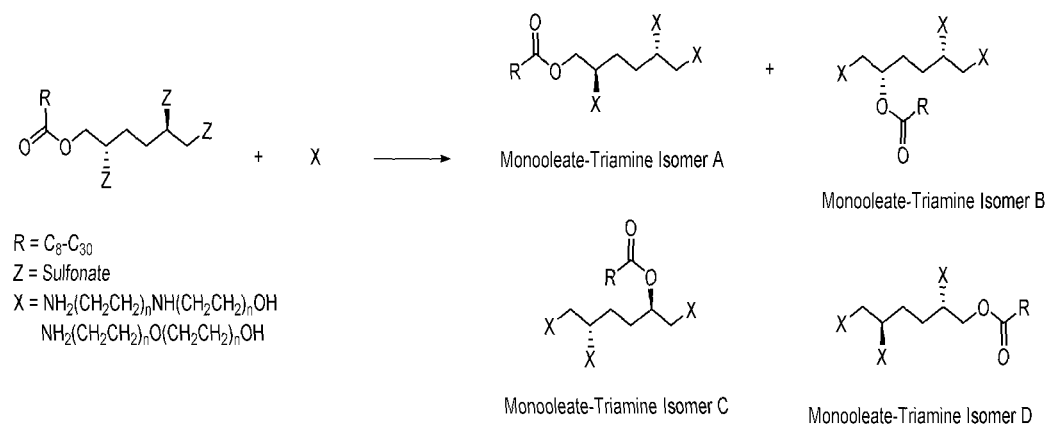
FIG. 4 depicts triflated (or sulfonated) 1,2,5,6-hexane esters undergoing nucleophilic displacement reactions with a hydrophilic amino reactant in an inert polar solvent, producing the targeted 1,2,5,6-hexane ester non-ionic amphiphiles.

In order to provide clear and consistent understanding of the specification and claims, including the scope to be given such terms, the following definitions are provided. It is also to be noted that the term "a" and "an" entity, refers to one or more or that entity; for example "a mild reducing agent," is understood to represent one or more mild reducing agents.

About. In the present application, including the claims, other than in the operating examples or where otherwise indicated, all numbers expressing quantities or characteristics are to be understood as being modified in all instances by the term "about". Accordingly, unless indicated to the contrary, any numerical parameters set forth in the following description may vary depending on the desired properties one seeks to obtain in the compositions and methods according to the present disclosure. At the very least, and not as an attempt to limit the application of the doctrine of equivalents to the scope of the claims, each numerical parameter described in the present description should at least be construed in light of the number of reported significant digits and by applying ordinary rounding techniques.

Ambient temperature. As used herein, the term ambient temperature refers to the temperature of the surroundings and will be the same as room temperature indoors.

Amphiphile. As used herein, the term amphiphile refers to a term describing a chemical compound possessing both hydrophilic (water-loving, polar) and lipophilic (fat-loving) properties. Such a compound is called amphiphilic or amphipathic.

Hydrophilic. As used herein, the term hydrophilic describes a compound having a tendency to mix with, dissolve in, or be wetted by water.

Overnight. As used herein, the term overnight refers to a time frame of between 10 and 20 hours, typically about 16 hours.

Neat. As used herein, the term neat refers to the absence of a solvent in a reaction.

Room temperature. As used herein, the term room temperature refers to a temperature that is between 20° C. and 26° C., with an average of about 23° C.

PTFE. As used herein refers to Polytetrafluoroethylene.

AEEA. As used herein refers to 2-((2-aminoethyl)amino) ethanol.

AEE. As used herein refers to 2-(2-aminoethoxy)ethanol.

DETAILED DESCRIPTION OF THE INVENTION

Derived primarily from sorbitol, the deoxygenated product 1,2,5,6-hexanetetrol is a reduced hexane polyol and embodies a versatile yet relatively unexplored substrate, owing to its commercial unattainability and serves as an example in this disclosure of a reduced hexane polyol. As a reagent, this molecular entity is attractive by virtue of its inherent chirality and tetrafunctionality, which enables multi-faceted, target orientated synthetic approaches to be effected in the generation of manifold materials with favorable chemical properties, such as polymer subunits, plasticizers, lubricants, dispersants, emulsifiers, adhesives coatings, resins, humectants and surfactants.

The present disclosure describes, in part, a highly efficient, three-step preparation of reduced hexane polyol based amphiphilic compound. For exemplary purposes, 1,2,5,6-hexanetetrol was used herein. Examples of other reduced hexane polyols include, but is not limited to mono-deoxygenated hexane polyols, di-deoxygenated hexane polyols, tri-deoxygenated hexane polyols, hexane glycols and hexanols. According to one embodiment of this disclosure, the process involves esterification of one or two of the —OH moieties with a fatty acid chloride containing 8-30 carbons carried out under ambient conditions in the presence of a nucleophilic base.

In the example of 1,2,5,6 hexanetetrol, the esterification is an alcohol acylation, which can be effectuated by several methods, including but not limited to Fischer esterification and Steglich esterification. The means used as exemplary in this disclosure entailed use of labile acid chlorides by Fischer esterification, however, any esterification method could be used.

Acid chloride acylation can result in copacetic yields of corresponding 1,2,5,6-hexane mono, di, tri, and tetra esters as manifest in the examples included herein.

The process is able to produce 1,2,5,6-hexane esters from one or more of the hydroxyl groups of 1,2,5,6 hexane tetrol in reasonably high molar yields of at least 95%, typically about 50% or 55% or 60-65% or 70%.

The esterification reaction is usually conducted in the temperature range of 0-50° C., typically 10° C. or 40° C., preferably 20 or 30° C., more preferably at about 25° C.

The esterification reaction requires a nucleophilic base to furnish high yields, such as dimethylaminopyridine, imidazole, and pyrazole, but preferably pyridine, owing to its facility of removal.

According to another embodiment, the vestigial —OH moieties of 1,2,5,6-hexanetetrol mono and di-esters are sulfonated with a sulfonating agent. The sulfonating agent is selected from the group consisting of p-toluenesulfonyl (tosyl), methanesulfonyl, (mesyl), ethanesulfonate (esyl), benzenesulfonate (besyl), p-bromobenzenesulfonate (brosyl), and triflouromethanesulfonic anhydride (triflate). For proof on concept in the present disclosure, the sulfonating agent trifluoromethanesulfonic anhydride was used.

The sulfonating reaction is conducted in an inert organic solvent with a high vapor pressure, such as chloroform, tetrahydrofuran, acetone, benzene, diethyl ether, but preferably methylene chloride and is conducted at temperatures between −20° C. and room temperature, typically between −10° C. and 10° C., but preferably at about 0° C.

The molar yields of 1,2,5,6-hexanetriflate esters is quantitative or near so.

According to an exemplary embodiment, a triflated sulfonated hexane ester undergoes a nucleophilic displacement reaction with a hydrophilic, primary amine in an inert polar solvent, producing the targeted non-ionic amphiphilic compound.

The hydrophilic primary amine is exemplified with AEE, and AEEA ($NH_2CH_2CH_2O$—, $NH_2CH_2CH_2NH$—) which contain sufficient internal oxygen, nitrogen atoms to render the final compound amphiphilic.

The nucleophilic substitution is conducted in an inert, polar solvent with a dielectric constant ($\in_r$>20), such as dimethylsulfoxide, dimethylformamide, dimethylacetamide, N-methylpyrrolidone, acetonitrile, methanol, ethanol, and acetone.

The reaction temperature is between 30° C. and 100° C., typically 40° C. and 80° C., preferably at about 50° C.

The molar yields of amphipathic 1,2,5,6-hexane esters are greater than about 50%, commonly 55-95%, preferably greater than 85%.

EXAMPLES

The following examples are furnished as demonstrative of the diverse aspects of the present disclosure, with the recognition that altering parameters and conditions, for example by change of temperature, time and reagent amounts, and particular starting species and catalysts and amounts thereof, can affect and extend the full practice of the invention beyond the limits of the examples presented.

The following examples refer to 1,2,5,6-hexanetetrol and limited fatty acids for reasons of facility; however, the scope of the invention is not necessarily relegated to those specific embodiments that introduce as other more common or commercially available fatty acid species. Example 1 divulges the synthesis of 1,2,5,6-hexane palmitate amphiphiles in three steps. Examples 2 shows the synthesis of 1,2,5,6-hexane oleate amphiphiles in three steps.

Example #1: Preparation of HTO-Palmitate Amphiphiles

Step #1 Synthesis and Isolation of HTO Mono, Di, Tri and Tetrapalmitates

Reaction scheme can be seen in FIG. 8

Experimental: A 100 mL round bottomed flask equipped with a PTFE magnetic stir bar was charged with 2.00 g of HTO (13.33 mmol), 10.98 g palmitoyl chloride (39.95 mmol, 3 eq), 10 mL of pyridine and 50 mL of chloroform. A reflux condenser was attached to the flask, and while vigorously stirring, the mixture was brought to reflux which persisted overnight. After this time, excess pyridine and chloroform were removed via rotary evaporation, leaving 12.43 g of a yellow syrup, which was taken up in a minimal amount of methylene chloride and charged to a pre-fabricated silica get column saturated with 100% hexanes. Flash chromatography with a gradient hexanes--->hexanes/ethyl acetate--->ethyl acetate--->ethyl acetate/methanol furnished four distinct fractions comprised of the following, with weights after drying: a) 0.58 g colorless loose oil, hexanetetrol tetrapalmitates (eluted 5:1 hexanes/ethyl acetate, TLC-cerium molybdate visualization, $R_f$=0.52 with 5:1 hexanes/ethyl acetate), $^1$H NMR (400 MHz, CDCl$_3$) δ (ppm) 5.03 (m, 2H), 4.60 (m, 2H), 4.10 (m, 2H), 2.22 (m, 8H), 1.71 (m, 8H), 1.26-1.19 (m, 100H), 0.94-0.91 (m, 12H); $^{13}$C NMR (100 MHz, CDCl$_3$) δ (ppm) 170.8, 170.6, 170.5, 72.6, 72.5, 66.4, 66.2, 35.1-28.3 (multiple signals, overlapped), 26.0, 25.8, 21.5, 21.4, 14.5, 14.3; b) 2.50 g pale yellow, loose oil, hexanetetrol tripalmitates (eluted 1:2 hexanes/ethyl acetate, TLC-cerium molybdate visualization, $R_f$=0.40-0.45 with 1:2 hexanes/ethyl acetate), $^1$H NMR (400 MHz, CDCl$_3$) δ (ppm) 5.06 (m, 1H), 4.99 (dd, J=8.2 Hz, J=8.0 Hz), 4.61 (m, 1H), 4.17 (d, J=12.2 Hz, 1H), 2.24 (m, 6H), 1.69 (m, 8H), 1.40-1.24 (m, 76H), 0.93-0.91 (m, 9H); $^{13}$C NMR (100 MHz, CDCl$_3$) δ (ppm) 170.7, 170.5, 170.4, 77.2, 69.9, 66.8, 35.0, 34.8, 34.7, 32.5-28.0 (multiple signals, overlapped), 26.1, 26.0, 25.9, 23.5, 23.3, 23.2, 14.3; c) 3.99 g colorless, viscous oil hexanetetrol dipalmitates (eluted 9:1 ethyl acetate/methanol, TLC-cerium molybdate visualization, $R_f$=0.32-0.39 with 9:1 ethyl acetate/methanol), $^1$H NMR (400 MHz, CDCl$_3$) δ (ppm) 5.56 (d, J=6.4 Hz, 1H), 5.27 (m, 1H), 4.98 (dd, J=8.2 Hz, J=8.0 Hz, 1H), 4.59 (J=12.0 Hz, J=7.6 Hz, 1H), 4.06 (dd, J=12.0 Hz, J=7.2 Hz, 1H), 3.56-3.50 (m, 3H), 2.25 (t, J=6.4 Hz, 2H), 2.23 (t, J=6.2 Hz, 2H), 1.69-1.66 (m, 4H), 1.52 (m, 1H), 1.43 (m, 1H), 1.40-1.29 (m, 48H), 0.92 (m, 6H); $^{13}$C NMR (100 MHz, CDCl$_3$) δ (ppm) 170.9, 170.7, 73.2, 72.9, 72.0, 64.1, 35.2, 35.0, 32.0-27.8 (multiple signals, overlapped), 26.0, 25.9, 23.1, 23.0, 14.5, 14.3; d) 2.55 g clear, viscous syrup hexanetetrol mono-palmitate (eluted 1:2 ethyl acetate/methanol, TLC-cerium molybdate visualization, $R_f$=0.27-0.30 with 1:2 ethyl acetate/methanol), $^1$H NMR (400 MHz, CDCl$_3$) δ (ppm) 5.41-5.37 (m, 2H), 4.96 (dd, J=8.3 Hz, J=8.1 Hz, 1H), 4.27 (J=12.0 Hz, J=7.2 Hz, 1H), 4.11 (m, 1H), 4.05 (dd, J=11.6 Hz, J=7.0 Hz, 1H), 3.55-3.51 (m, 3H), 2.25 (t, J=6.2 Hz, 2H), 1.65 (dt, J=6.4 Hz, J=6.0 Hz, 2H), 1.40-1.31 (m, 30H), 0.90 (t, J=6.4 Hz, 3H); $^{13}$C NMR (100 MHz, CDCl$_3$) δ (ppm) 171.2, 73.0, 72.2, 72.0, 68.4, 34.0, 32.1, 30.4, 30.3, 30.2, 30.1, 30.0, 29.8, 29.6, 29.5, 29.4, 29.2, 28.4, 28.1, 23.1, 14.4.

Step #2 Triflation of HTO Mono and Dipalmitates
Reaction scheme can be seen in FIG. 9
Experimental (furnished with dipalmitates): An oven-dried 100 mL round bottomed flask was charged with 2.00 g of a HTO-dipalmitate mixture (3.34 mmol), 5 mL of anhydrous pyridine and 50 mL of anhydrous methylene chloride. The homogeneous solution was cooled to ~0° C. in an ice bath. While stirring, 1.40 mL of triflic anhydride (8.35 mmol) was added dropwise over 5 minutes. Once added, the ice bath was removed and sulfonation reaction continued overnight. After this time, excess triflic anhydride was quenched by adding 2 mL of water, and the mixture charged directly to a pre-fabricated silica gel column, where flash chromatography with a gradient hexanes/ethyl acetate eluent furnished 2.22 g of a light yellow oil, representing the triflated analogs of HTO-dipalmitates (77%), $^1$H NMR (400 MHz, CDCl$_3$) δ (ppm) 5.25 (m, 1H), 4.92 (m, 2H), 4.36 (dd, J=11.8 Hz, J=7.0 Hz, 1H), 4.20 (d, J=12.2 Hz, J=6.8 Hz, 1H), 4.08 (d, J=12.0 Hz, J=6.9 Hz, 1H), 3.91 (dd, J=12.1 Hz, J=7.0 Hz, 1H), 2.40 (t, J=6.2 Hz, 2H), 2.32 (t, J=6.4 Hz, 2H), 1.68-1.66 (m, 4H), 1.71 (m, 4H), 1.40-1.32 (m, 52H), 0.93-0.91 (m, 6H); $^{13}$C NMR (100 MHz, CDCl$_3$) δ (ppm) 171.4, 171.2, 120.1, 119.8, 87.0, 72.2, 71.4, 66.7, 35.3, 34.8, 32.2-28.1 (multiple signals, overlapped), 25.9, 25.0, 24.4, 24.0, 22.1, 14.3, 14.2.

Step #3 AEEA-Derivitized HTO Mono and Dipalmitates
Reaction scheme can be seen in FIG. 10
Experimental (example with HTO dipalmitate ditriflates): A 250 mL round bottomed flask equipped with a PTFE magnetic stir bar was charged with 2.00 g of a HTO dipalmitate tritriflate mixture (2.24 mmol), 701 mg of 2-((2-aminoethyl)amino)ethan-1-ol (AEEA, 6.73 mmol) and 100 mL of absolute ethanol. A reflux condenser was affixed to the flask and, while vigorously stirring, the mixture was held at reflux for 4 h. After this time, the orange solution was charged to a pre-fabricated column dry-packed with neutral alumina. Flash chromatography isocratic with ethanol furnished 1.28 g of the title compound as a viscous pale yellow oil (72%), $^1$H NMR (400 MHz, CD$_3$OD) δ (ppm) 5.22 (t, J=6.8 Hz, 1H), 4.52 (dd, J=12.1 Hz, J=7.0 Hz, 1H), 4.08 (dd, J=12.2 Hz, J=7.1 Hz, 1H), 3.60 (t, J=6.6 Hz, 4H), 2.72-2.66 (m, 10H), 2.48 (m, 2H), 2.38 (t, J=6.0 Hz, 2H), 1.72 (dt, J=8.2 Hz, J=4.6 Hz, 2H), 1.69 (dt, J=7.9 Hz, J=4.8 Hz, 2H), 1.58 (t, J=7.2 Hz, 2H), 1.40-1.31 (m, 50H), 0.93 (t, J=7.2 Hz, 3H), 0.90 (t, J=7.0 Hz, 3H); $^{13}$C NMR (100 MHz, CD$_3$OD) δ (ppm) 172.1, 171.8, 72.1, 66.7, 62.5, 62.3, 59.4, 55.1, 52.7, 52.5, 51.0, 50.8, 50.5, 50.4, 47.3, 35.1, 34.9, 32.0-27.9 (multiple signals, overlapped), 27.1, 26.9, 26.1, 25.8, 23.3, 23.1, 14.3, 14.2.

Example #2: Preparation and Isolation of HTO-Oleate Amphiphiles

Step #1 Synthesis and Isolation of HTO Mono, Di, Tri and Tetraoleates
Reaction scheme can be seen in FIG. 11
Experimental: A 100 mL round bottomed flask equipped with a PTFE magnetic stir bar was charged with 2.00 g of HTO (13.33 mmol), 12.03 g oleoyl chloride (39.95 mmol, 3 eq), 10 mL of pyridine and 50 mL of chloroform. A reflux condenser was attached to the flask, and while vigorously stirring, the mixture was brought to reflux which persisted overnight. After this time, excess pyridine and chloroform were removed via rotary evaporation, affording 12.77 g of a yellow syrup, which was taken up in a minimal amount of methylene chloride and charged to a pre-fabricated silica gel column saturated with 100% hexanes. Flash chromatography with a gradient hexanes--->hexanes/ethyl acetate--->ethyl acetate--->ethyl acetate/methanol furnished four distinct fractions comprised of the following, with weights after drying: a) 0.71 g colorless loose oil, hexanetetrol tetraoleates (eluted 6:1 hexanes/ethyl acetate, TLC-cerium molybdate visualization, $R_f$=0.57 with 6:1 hexanes/ethyl acetate), $^1$H NMR (400 MHz, CDCl$_3$) δ (ppm) 5.42-5.38 (m, 8H), 5.24-5.22 (m, 4H), 4.49-4.47 (m, 4H), 4.25-4.23 (m, 4H), 2.40-2.36 (m, 8H), 2.25-2.20 (m, 16H), 1.71-1.68 (m, 8H), 1.56 (t, J=6.2 Hz, 2H), 1.53 (t, J=6.4 Hz, 2H), 1.35-1.26 (m, 80H), 0.93-0.90 (m, 12H); $^{13}$C NMR (100 MHz, CDCl$_3$) δ (ppm) 172.2, 172.1, 172.0, 132.1, 132.0, 131.8, 131.7, 131.5, 131.3, 72.1, 71.9, 67.3, 66.9, 34.1-28.5 (multiple signals, overlapped), 26.1, 25.9, 25.6, 25.5, 25.3, 23.1, 22.9, 22.8, 22.6, 14.5, 14.3; b) 2.13 g clear loose oil, hexanetetrol trioleates (eluted 1:1 hexanes/ethyl acetate, TLC-cerium molybdate visualization, $R_f$=0.44-0.48 with 1:1 hexanes/ethyl acetate), $^1$H NMR (400 MHz, CDCl$_3$) δ (ppm) 5.42-5.39 (m, 6H), 5.30 (d, J=6.8 Hz, 1H), 5.05 (m, 1H), 4.46 (dd, J=12.4 Hz, J=7.2 Hz, 1H), 4.38 (dd, J=12.2 Hz, J=7.0 Hz, 1H), 4.15-4.11 (m, 3H), 2.40-2.37 (m, 6H), 2.24-2.21 (m, 12H), 1.73-1.70 (m, 6H), 1.54 (t, J=6.6

Hz, 1H), 1.51 (t, J=6.0 Hz, 1H), 1.36-1.28 (m, 66H), 0.92-0.90 (m, 9H); $^{13}$C NMR (100 MHz, CDCl$_3$) δ (ppm) 172.0, 171.8. 171.7, 132.2, 132.0, 131.9, 131.8, 131.7, 72.3, 72.0, 71.8, 67.2, 34.1-28.5 (multiple signals, overlapped), 27.9, 26.1, 23.3, 23.1, 22.9, 14.5, 14.3, 14.2; c) 4.38 g colorless, viscous oil hexanetetrol dioleates (eluted 11:1 ethyl acetate/methanol, TLC-cerium molybdate visualization, R$_f$=0.40-0.43 with 11:1 ethyl acetate/methanol), $^1$H NMR (400 MHz, CDCl$_3$) δ (ppm) 5.44 (dd, J=10.2 Hz, J=4.2 Hz, 1H), 5.40 (dd, J=10.1 Hz, J=4.0 Hz, 1H), 5.36 (dd, J=10.0 Hz, J=4.4 Hz, 1H), 5.35 (dd, J=10.2 Hz, J=4.3 Hz, 1H), 5.32 (d, J=6.5 Hz, 1H), 4.94 (dd, J=12.2 Hz, J=7.0 Hz, 1H), 4.71 (m, 1H), 4.42 (dd, J=12.3 Hz, J=7.0 Hz, 1H), 4.11-4.08 (m, 2H), 3.77 (dd, J=12.0, J=4.0 Hz, 1H), 3.71 (dd, J=11.8, J=4.3 Hz, 1H), 2.41 (t, J=6.6 Hz, 2H), 2.36 (t, J=6.4 Hz, 2H), 2.22-2.18 (m, 8H), 1.72-1.69 (m, 4H), 1.52 (t, J=6.2 Hz, 1H), 1.42 (dt, J=6.8 Hz, J=4.4 Hz, 2H), 1.34-1.29 (m, 40H), 0.92 (t, J=6.2 Hz, 3H), 0.88 (t, J=6.4 Hz, 3H); $^{13}$C NMR (100 MHz, CDCl$_3$) δ (ppm) 172.0, 171.8, 132.3, 132.3, 132.0, 131.9, 74.0, 71.9, 71.7, 67.4, 34.0, 33.6, 32.9-28.7 (multiple signals, overlapped), 26.0, 25.8, 23.1, 22.5, 22.0, 14.5, 14.1; d) 2.81 g clear, viscous oil hexanetetrol monooelates (eluted 1:1 ethyl acetate/methanol, TLC-cerium molybdate visualization, R$_f$=0.30-0.33 with 1:1 ethyl acetate/methanol). $^1$H NMR (400 MHz, CDCl$_3$) δ (ppm) 5.43 (dd, J=10.1 Hz, J=4.4 Hz, 1H), 5.41 (dd, J=10.3 Hz, J=4.2 Hz, 1H), 5.31 (d, J=6.8 Hz, 1H), 5.25 (d, J=6.6 Hz, 1H), 4.91 (d, J=6.2 Hz, 1H), 4.40 (dd, J=12.0 Hz, J=7.2 Hz, 1H) 4.09-4.07 (m, 2H) 3.55-3.49 (m, 3H), 2.41 (t, J=6.4 Hz, 2H), 2.20-2.18 (m, 4H), 1.71 (dt, J=7.2 Hz, J=7.0 Hz, 2H), 1.43 (m, 4H), 1.32-1.28 (m, 20H), 0.93 (t, J=6.4 Hz, 3H); $^{13}$C NMR (100 MHz, CDCl$_3$) δ (ppm) 172.1, 132.0, 131.8, 73.6, 72.0, 67.3, 33.7, 32.1, 31.9, 31.8, 31.6, 31.4, 31.3, 31.1, 29.0, 28.5, 28.4, 28.2, 26.2, 23.2, 14.4.

Step #2 Triflation of HTO Mono and Dioleates

Reaction scheme can be seen in FIG. 12

Experimental (example with HTO monooleates): An oven-dried 100 mL round bottomed flask was charged with 2.00 g of a HTO-monooleate mixture (4.82 mmol), 5 mL of anhydrous pyridine and 50 mL of anhydrous methylene chloride. The homogeneous solution was cooled to ~0° C. in an ice bath. While stirring, 3.25 mL of triflic anhydride (19.3 mmol) was added dropwise over 5 minutes. Once added, the ice bath was removed and sulfonation reaction continued overnight. After this time, excess triflic anhydride was quenched by adding 2 mL of water, and the mixture charged directly to a pre-fabricated silica gel column, where flash chromatography with a gradient hexanes/ethyl acetate eluent furnished 3.13 g of a light yellow oil, representing the triflated analogs of HTO-monooleates (80%). $^1$H NMR (400 MHz, CDCl$_3$) δ (ppm) 5.47 (dd, J=10.3 Hz, J=4.0 Hz, 1H), 5.41 (dd, J=10.5 Hz, J=4.4 Hz, 1H), 5.38 (m, 1H), 4.91 (m, 1H), 4.40 (dd, J=12.2 Hz, J=6.1 Hz, 1H), 4.21 (dd, J=12.0 Hz, J=6.4 Hz, 1H), 4.16 (dd, J=12.1 Hz, J=6.6 Hz, 1H), 3.92 (dd, J=11.9 Hz, J=6.4 Hz, 1H), 2.40 (t, J=6.5 Hz, 2H), 2.19-2.16 (m, 4H), 1.70 (dt, J=7.2 Hz, J=7.0 Hz, 2H), 1.45 (m, 4H), 1.32-1.28 (m, 20H), 0.92 (t, J=6.2 Hz, 3H); $^{13}$C NMR (100 MHz, CDCl$_3$) δ (ppm) 171.9, 130.9, 130.7, 120.1, 119.9, 119.7, 88.0, 87.4, 71.7, 68.1, 34.6, 32.4, 31.5, 31,4, 31.2, 30.9, 30.7, 30.5, 30.3, 29.0, 28.8, 26.1, 25.5, 25.2, 23.5, 14.6.

Step #3 AEE Derivitized HTO Mono and Dioleates

Reaction scheme can be seen in FIG. 13

Experimental (with HTO monoleate, tritriflate): A 250 mL round bottomed flask equipped with a PTFE magnetic stir bar was charged with 2.00 g of a HTO monooleate, tritriflate mixture (2.47 mmol), 1.03 g of 2-((2-aminoethyl)amino) ethan-1-ol (AEEA, 9.87 mmol) and 100 mL of absolute ethanol. A reflux condenser was affixed to the flask and, while vigorously stirring, the mixture was held at reflux for 4 h. After this time, the orange solution was charged to a pre-fabricated column dry-packed with neutral alumina. Flash chromatography isocratic with ethanol furnished 1.24 g of the title compound as a viscous, clear oil (74%). $^1$H NMR (400 MHz, CD$_3$OD) δ (ppm) 5.44 (dd, J=10.2 Hz, J=4.4 Hz, 1H), 5.41 (dd, J=10.0 Hz, J=4.6 Hz, 1H), 4.41 (dd, J=12.2 Hz, J=6.8 Hz, 1H), 3.92 (dd, J=12.0 Hz, J=6.5 Hz, 1H), 3.60 (t, J=6.2 Hz, 2H), 3.56 (t, J=6.0 Hz, 2H), 3.54 (t, J=6.0 Hz, 2H), 3.16 (dt, J=7.2 Hz, J=7.0 Hz, 1H), 2.74-2.66 (m, 14H), 2.55-2.51 (m, 4H), 2.40 (t, J=6.2 Hz), 2.20-2.18 (m, 4H), 1.71 (dt, J=7.4 Hz, J=7.2 Hz, 2H), 1.36-1.28 (m, 24H), 0.92 (t, J=6.9 Hz, 3H); $^{13}$C NMR (100 MHz, CD$_3$OD) δ (ppm) 172.1, 131.1, 130.9, 69.6, 62.9, 62.5, 62.3, 60.9, 59.1, 54.8, 53.0, 52.9, 52.8, 50.5, 50.3, 50.1, 49.9, 48.0, 47.6, 35.1, 32.6, 32.0, 31.8, 31.0, 30.8, 30.6, 30.0, 29.6, 28.9, 28.7, 27.3, 25.9, 23.5, 14.0.

What is claimed is:

1. A method of making an amphiphilic compound selected from the group consisting of:

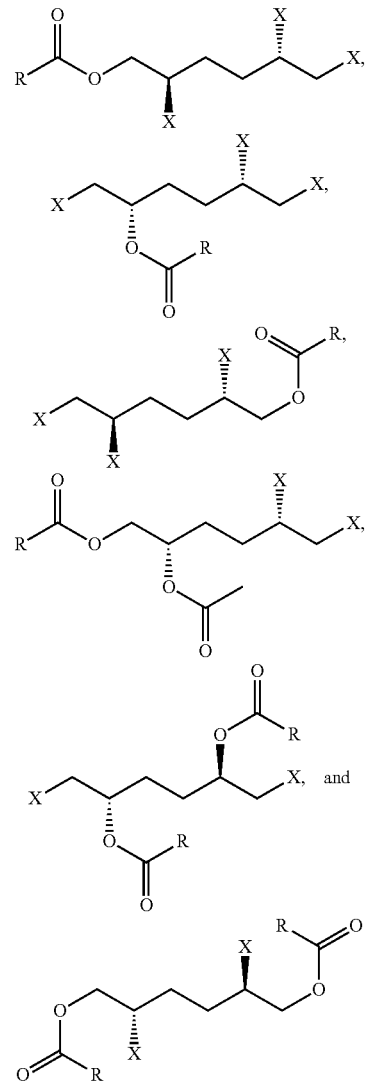

comprising contacting a sulfonate ester moiety of a sulfonated hexane ester with a primary amine to displace said sulfonate ester moiety with the primary amine, wherein X is a primary amine and R is a carbon side chain of a fatty acid with between 8 and 30 carbons.

2. The method of claim 1, further comprising said contacting is done in the presence of polar solvent selected from the group consisting of dimethylsulfoxide, dimethylformamide, dimethylacetamide, N-methylpyrrolidone, acetonitrile, methanol, ethanol, and acetone.

3. The method of claim 1, wherein said sulfonate ester moiety is contacted with said primary amine at a temperature from about 30° C. to about 100° C.

4. The method of claim 1, wherein said sulfonate ester moiety is contacted with said primary amine at a temperature of about 50° C.

* * * * *